(12) United States Patent
Khamidulin et al.

(10) Patent No.: US 11,578,020 B2
(45) Date of Patent: Feb. 14, 2023

(54) NAPHTHA COMPLEX WITH THERMAL OXIDATION SYSTEM

(71) Applicant: Honeywell International Inc., Morris Plains, NJ (US)

(72) Inventors: Eldar Khamidulin, Guildford (GB); Jan De Ren, Bracknell (GB); Raymond S. Chan, Ottershaw (GB); William J. Whyman, Tulsa, OK (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 17/361,685

(22) Filed: Jun. 29, 2021

(65) Prior Publication Data

US 2022/0041527 A1    Feb. 10, 2022

Related U.S. Application Data

(60) Provisional application No. 63/060,803, filed on Aug. 4, 2020.

(51) Int. Cl.
*C07C 7/00* (2006.01)
*C07C 5/27* (2006.01)
(Continued)

(52) U.S. Cl.
CPC ............. *C07C 7/005* (2013.01); *B01D 3/143* (2013.01); *B01D 53/1481* (2013.01);
(Continued)

(58) Field of Classification Search
CPC ......... C07C 7/005; C07C 5/2702; C07C 7/04; B01D 3/143; B01D 53/1481;
(Continued)

(56) References Cited

U.S. PATENT DOCUMENTS 3,567,433 A    3/1971 Gutnikov
4,377,470 A    3/1983 Hettinger, Jr. et al.
(Continued)

FOREIGN PATENT DOCUMENTS

CA    2706957 A1    6/2009
CN    101239758 A    8/2008
(Continued)

OTHER PUBLICATIONS

Levy, Edward et al., Recovery of Water from Boiler Flue Gas Using Condensing Heat Exchangers, Final Technical Report issued Jun. 2011, Energy Research Center.
(Continued)

*Primary Examiner* — Thuan D Dang

(57) ABSTRACT

A process for treating effluent streams in a naphtha complex is described. One or more of the sour water stripping unit for the NHT sour water from the NHT, the amine treatment unit and the caustic treatment unit for the NHT stripper off-gas, the caustic scrubber unit or other chloride treatment unit for the off-gas from the $C_5$-$C_6$ isomerization zone and the $C_4$ isomerization zone, and the caustic scrubber unit or other chloride treatment unit for the regenerator off-gas are replaced with a thermal oxidation system.

20 Claims, 4 Drawing Sheets

(51) Int. Cl.
*C10G 61/02* (2006.01)
*C10G 69/08* (2006.01)
*B01D 53/86* (2006.01)
*B01D 53/34* (2006.01)
*B01D 53/68* (2006.01)
*B01D 53/50* (2006.01)
*B01D 53/78* (2006.01)
*B01D 53/14* (2006.01)
*B01D 53/72* (2006.01)
*B01D 53/96* (2006.01)
*C02F 1/72* (2023.01)
*C02F 1/02* (2023.01)
*B01D 3/14* (2006.01)
*C07C 7/04* (2006.01)

(52) U.S. Cl.
CPC ....... *B01D 53/1493* (2013.01); *B01D 53/343* (2013.01); *B01D 53/502* (2013.01); *B01D 53/68* (2013.01); *B01D 53/72* (2013.01); *B01D 53/78* (2013.01); *B01D 53/8625* (2013.01); *B01D 53/8668* (2013.01); *B01D 53/96* (2013.01); *C02F 1/02* (2013.01); *C02F 1/72* (2013.01); *C07C 5/2702* (2013.01); *C07C 7/04* (2013.01); *C10G 61/02* (2013.01); *C10G 69/08* (2013.01); *B01D 2251/304* (2013.01); *B01D 2251/402* (2013.01); *B01D 2251/404* (2013.01); *B01D 2252/102* (2013.01); *B01D 2257/2025* (2013.01); *B01D 2257/2045* (2013.01); *B01D 2257/302* (2013.01); *B01D 2257/404* (2013.01); *B01D 2257/70* (2013.01); *C10G 2300/1044* (2013.01); *C10G 2300/202* (2013.01); *C10G 2300/207* (2013.01); *C10G 2300/70* (2013.01); *C10G 2400/20* (2013.01); *C10G 2400/30* (2013.01)

(58) Field of Classification Search
CPC .............. B01D 53/1493; B01D 53/343; B01D 53/502; B01D 53/68; B01D 53/72; B01D 53/78; B01D 53/8625; B01D 53/8668; B01D 53/96; B01D 2251/304; B01D 2251/402; B01D 2251/404; B01D 2252/102; B01D 2257/2025; B01D 2257/2045; B01D 2257/302; B01D 2257/404; B01D 2257/70; B01D 53/75; B01D 2251/206; B01D 2255/20707; B01D 2255/20723; B01D 2255/20776; B01D 2258/0283; C02F 1/02; C02F 1/72; C02F 1/04; C02F 2103/365; C10G 61/02; C10G 69/08; C10G 2300/1044; C10G 2300/202; C10G 2300/207; C10G 2300/70; C10G 2400/20; C10G 2400/30

See application file for complete search history.

(56) References Cited

U.S. PATENT DOCUMENTS

| | | | |
|---|---|---|---|
| 4,430,517 A | 2/1984 | Imai et al. | |
| 4,514,368 A | 4/1985 | Hubred | |
| 4,544,533 A | 10/1985 | Marcantonio | |
| 4,762,812 A | 8/1988 | Lopez et al. | |
| 5,339,755 A | 8/1994 | Smith | |
| 5,365,010 A | 11/1994 | Rao et al. | |
| 6,449,954 B2 | 9/2002 | Bachmann | |
| 6,514,904 B1 | 2/2003 | Moser et al. | |
| 7,002,048 B2 | 2/2006 | Wijesekera et al. | |
| 7,034,192 B2 | 4/2006 | Wijesekera | |
| 7,126,029 B2 | 10/2006 | Skipworth et al. | |
| 7,141,700 B1 | 11/2006 | Schmidt et al. | |
| 7,141,701 B1 | 11/2006 | Schmidt et al. | |
| 7,166,752 B2 | 1/2007 | Marshall, Jr. et al. | |
| 7,186,866 B1 | 3/2007 | Keenan et al. | |
| 7,417,003 B2 | 8/2008 | Schmidt et al. | |
| 7,674,739 B2 | 3/2010 | Elomari et al. | |
| 7,652,181 B1 | 4/2010 | Schmidt et al. | |
| 7,700,511 B2 | 4/2010 | Reynolds et al. | |
| 7,740,751 B2 | 6/2010 | Peters | |
| 7,744,828 B2 | 6/2010 | Schmidt et al. | |
| 7,841,807 B2 | 11/2010 | Naunheimer et al. | |
| 7,878,736 B2 | 2/2011 | Naunheimer et al. | |
| 7,888,537 B2 | 2/2011 | Schmidt et al. | |
| 8,242,320 B2 | 8/2012 | Schmidt et al. | |
| 8,329,603 B2 | 12/2012 | Randolph et al. | |
| 8,387,645 B2 | 3/2013 | Shafe | |
| 8,457,278 B2 | 6/2013 | Fadler | |
| 8,518,847 B2 | 8/2013 | Jan et al. | |
| 8,608,941 B2 | 12/2013 | Haizmann et al. | |
| 8,609,915 B2 | 12/2013 | Majumdere et al. | |
| 8,609,916 B2 | 12/2013 | Majumder et al. | |
| 8,679,321 B2 | 3/2014 | Negiz et al. | |
| 8,853,481 B2 | 10/2014 | Jan et al. | |
| 9,006,123 B2 | 4/2015 | Nabozny | |
| 9,079,816 B2 | 7/2015 | Johnson et al. | |
| 9,138,738 B1 | 9/2015 | Glover et al. | |
| 9,150,469 B2 | 10/2015 | Bullen et al. | |
| 9,181,150 B1 | 11/2015 | Smith et al. | |
| 9,206,362 B2 | 12/2015 | Haizmann et al. | |
| 9,290,826 B2 | 3/2016 | Da Costa et al. | |
| 9,302,951 B2 | 4/2016 | Stevens et al. | |
| 9,321,783 B2 | 4/2016 | Ibert et al. | |
| 9,327,259 B2 | 5/2016 | Hartman et al. | |
| 9,328,037 B2 | 5/2016 | Riley et al. | |
| 9,359,917 B2 | 6/2016 | Koseoglu et al. | |
| 9,360,252 B2 | 6/2016 | Furlong et al. | |
| 9,399,604 B2 | 7/2016 | Martins et al. | |
| 9,416,321 B2 | 8/2016 | Eizenga et al. | |
| 9,469,818 B2 | 10/2016 | Baldriaghi et al. | |
| 9,523,050 B2 | 12/2016 | Pandranki et al. | |
| 9,567,264 B2 | 2/2017 | Fichtl | |
| 9,637,699 B2 | 5/2017 | Ellig et al. | |
| 9,718,047 B2 | 8/2017 | Moser et al. | |
| 9,745,523 B2 | 8/2017 | Ganguly et al. | |
| 9,815,756 B2 | 11/2017 | Schmidt et al. | |
| 9,822,314 B2 | 11/2017 | Ray | |
| 9,914,675 B2 | 3/2018 | Buchbinder et al. | |
| 9,914,880 B2 | 3/2018 | Fichtl et al. | |
| 9,914,883 B2 | 3/2018 | Dutta et al. | |
| 10,041,004 B2 | 8/2018 | Govindhakannan et al. | |
| 10,240,099 B2 | 3/2019 | Mani et al. | |
| 10,384,186 B2 | 8/2019 | Egolf et al. | |
| 10,399,852 B2 * | 9/2019 | De Ren | B01D 53/1462 |
| 10,429,066 B2 | 10/2019 | Schröter et al. | |
| 10,577,539 B2 | 3/2020 | Brodeur-Campbell et al. | |
| 10,577,547 B2 | 3/2020 | Wexler et al. | |
| 2005/0172807 A1 | 8/2005 | Mak | |
| 2013/0087481 A1 | 4/2013 | Heraud et al. | |
| 2013/0284019 A1 | 10/2013 | Gstoettenmayr et al. | |
| 2015/0094486 A1 | 4/2015 | Buchbinder et al. | |
| 2016/0168054 A1 | 6/2016 | Kalnes et al. | |
| 2019/0144766 A1 | 5/2019 | Yokomizo et al. | |
| 2019/0292949 A1 | 9/2019 | Sonnek et al. | |
| 2020/0222851 A1 | 7/2020 | De Ren et al. | |
| 2021/0270957 A1 | 9/2021 | Zhu et al. | |

FOREIGN PATENT DOCUMENTS

| | | |
|---|---|---|
| EP | 0320094 A2 | 6/1989 |
| EP | 1218890 A2 | 7/2002 |
| WO | 2016004473 A1 | 1/2016 |

OTHER PUBLICATIONS

Liu, Xinpeng et al., Desulfurization and regeneration performance of heteropoly compound/ionic liquid solutions at high temperature, Chemical Engineering Journal 316, 2017, 171-178.

I.M. Mukhametgaliev et al., Purification of gases from acidic components, Technological University Bulletin [online], 2017, vol.

(56) References Cited

OTHER PUBLICATIONS

20, No. 3, found on the internet: <URL: https://cyberleninka.ru/article/n/17069859.pdf> (abstract only).
International Search Report from corresponding PCT application No. PCT/US2021/017071 dated Nov. 3, 2021.
Written Opinion from corresponding PCT application No. PCT/US2021/017071 dated Nov. 3, 2021.

* cited by examiner

NAPHTHA COMPLEX WITH THERMAL OXIDATION SYSTEM

RELATED APPLICATIONS

This application claims the benefit of U.S. Provisional Patent Application Ser. No. 63/060,803 filed on Aug. 4, 2020, the entirety of which is incorporated herein by reference.

BACKGROUND

A traditional naphtha complex may include a naphtha hydrotreater (NHT) zone, a $C_5$-$C_6$ isomerization zone, a catalytic reforming zone, and in some cases a $C_4$ isomerization zone. There are several effluent streams produced in the naphtha complex having these zones that require treatment. NHT sour water from the NHT is sent to a sour water stripping unit. The NHT stripper off-gas stream is typically sent to an amine treating unit to remove $H_2S$. Off-gas from the $C_5$-$C_6$ isomerization zone and the $C_4$ isomerization zone is typically sent to a caustic scrubber to remove chlorine-containing species or to another chloride treatment unit for removing chlorine-containing species from a hydrocarbon-containing vapor stream with a fluid hydrocarbon sorbent of the $C_5$-$C_6$ isomerization zone and the $C_4$ isomerization zone. Regenerator off-gas from the regeneration of the reforming catalyst can either be sent to a caustic scrubber to remove chlorine-containing species or can be recycled to the catalyst regeneration zone for the catalyst to sorb the chlorine-containing species from the gas before being released to the atmosphere.

Treatment of these effluent streams requires chemicals, as well as additional capital and operating costs for the amine treating unit, the caustic scrubber units or the chloride treatment equipment. In addition, in some situations, the treatment and circulation of the off-gases can result in corrosion problems in the naphtha complex.

Chloride treatment may also require vent gas chloride treating units in order to meet environmental regulations. This may result in solid waste from the sorbent used in the vent gas chloride treating units which must be disposed of.

Moreover, these treatments may not be sufficient to meet increasingly stringent environmental regulations.

Therefore, there is a need for an improved process for treating effluent streams in a naphtha complex.

DESCRIPTION OF THE INVENTION

Figure 1:
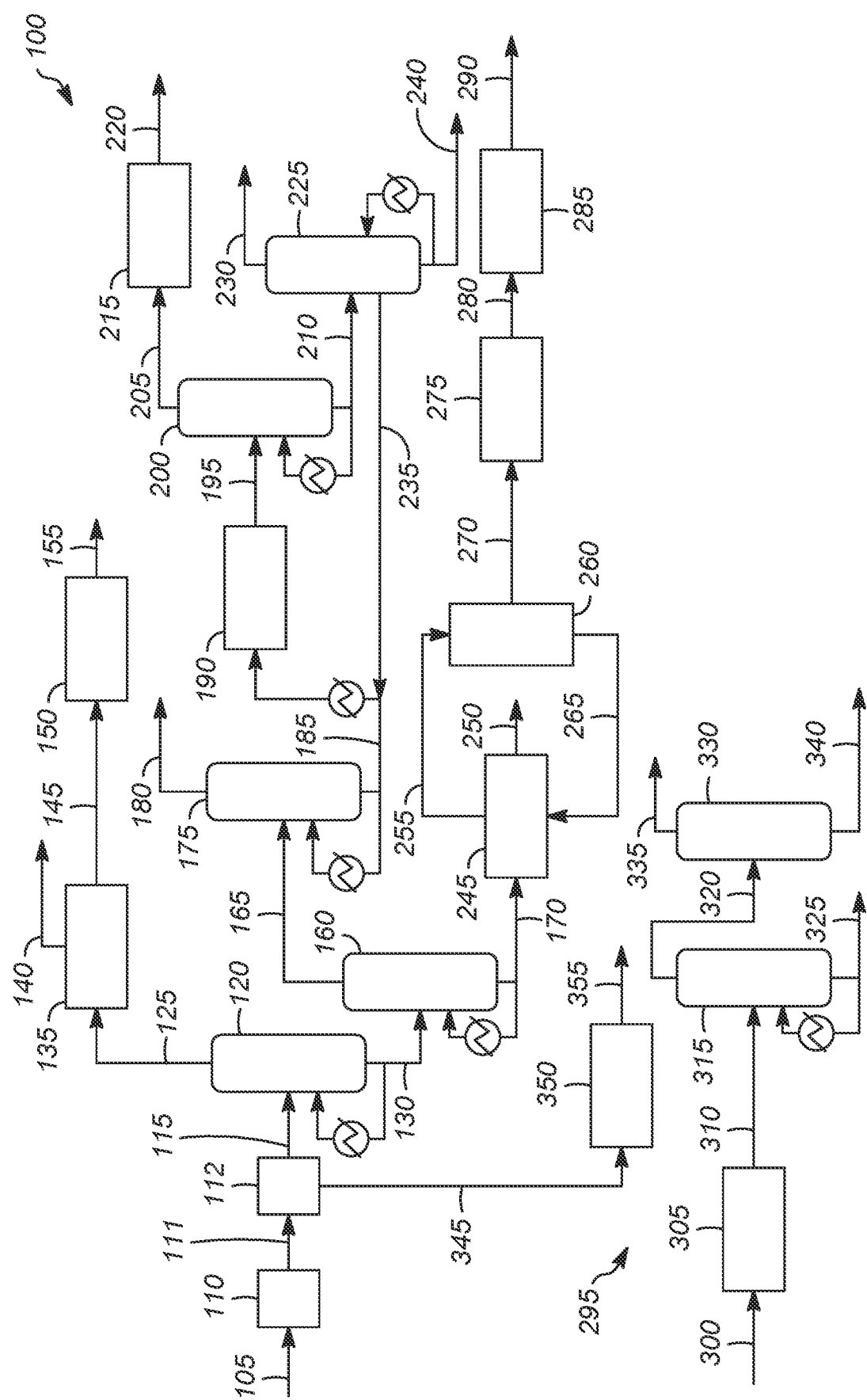
FIG. 1 is an illustration of one embodiment of a naphtha complex.

The present invention relates to a process for treating effluent streams in a naphtha complex. One or more of the sour water stripping unit for the NHT sour water from the NHT, the amine treatment unit or the caustic treatment unit for the NHT stripper off-gas, the caustic scrubber unit or other chloride treatment unit for the off-gas from the $C_5$-$C_6$ isomerization zone and the $C_4$ isomerization zone, and the caustic scrubber unit or other chloride treatment unit for the regenerator off-gas can be replaced with a thermal oxidation system. The elimination of several process units with their associated equipment decreases the capital costs. The operating costs are reduced as a result of decreasing or eliminating the corrosion problems and environmental issues.

By eliminating the need for an amine treatment unit, the need to treat the amine unit regenerator acid gas stream is also avoided. Currently, the amine unit regenerator acid gas stream is typically sent to a sulfur recovery unit or a thermal oxidizer and in some cases, a caustic scrubber. This avoids the potential for the sulfur treatment to be a bottleneck for the naphtha complex. For example, product specifications might require a higher level of hydrotreating, which would generate additional $H_2S$, increasing the load on the sulfur treatment. This problem may be reduced or avoided altogether with the present process.

Additionally, energy costs are reduced as a result of optional waste heat recovery. Waste heat can be recovered in the form of steam, hot oil, electricity, or combinations thereof. The steam and/or hot oil and/or electricity can be used to supply heat requirements in various pieces of equipment in the naphtha/$C_4$ isomerization complex or elsewhere. This includes, but is not limited to, preheating to gas in the continuous catalyst regeneration zone, or reboiler duty requirements. Reboilers which could utilize the recovered waste heat in the form of steam or hot oil include, but are not limited to, the naphtha hydrotreater (NHT) stripper column, the de-isopentanizer column, the naphtha splitter column, the $C_5$-$C_6$ isomerization stabilizer column, the de-isohexanizer column, and the $C_4$ isomerization stabilizer column. Waste heat recovered in the form of electricity can be used in the electrical heaters of the continuous catalyst regeneration zone for gas preheating, for example.

One aspect of the invention is a process for treating off-gas and water effluent streams in a naphtha complex. In one embodiment, the process comprises: thermally oxidizing at least one of a NHT stripper off-gas stream from a NHT stripper column, a $C_5$-$C_6$ isomerization stabilizer off-gas stream from a $C_5$-$C_6$ isomerization stabilizer column, a regenerator off-gas stream from a catalyst regenerator zone of a reforming zone, a $C_4$ isomerization stabilizer off-gas stream from a $C_4$ isomerization stabilizer column, and a NHT sour water stream from a NHT product separator in a thermal oxidation system. This comprises: thermally oxidizing the at least one of the NHT stripper off-gas stream, the $C_5$-$C_6$ isomerization stabilizer off-gas stream, the regenerator off-gas stream, the $C_4$ isomerization stabilizer off-gas stream, and the NHT sour water stream in a thermal oxidizing section forming flue gas consisting essentially of at least one of $H_2O$, $CO_2$, $N_2$, $O_2$, SOx, NOx, HCl, $Cl_2$, dioxins, and furans. Optionally waste heat is recovered from the flue gas in an optional waste heat recovery section. At least one of SOx, HCl, and $Cl_2$ is removed from the flue gas in a SOx removal section to form a de-SOx outlet flue gas consisting essentially of at least one of $H_2O$, $CO_2$, $N_2$, $O_2$, NOx, dioxins, and furans. The removal of at least one of SOx, HCl, and $Cl_2$ comprises: quenching the flue gas in a quench section to form quenched flue gas after recovering the waste heat; and contacting a caustic solution or an $NH_3$ based solution with the quenched flue gas in scrubbing section to form the de-SOx outlet flue gas and a liquid stream comprising at least one of $H_2O$, $Na_2SO_3$, $Na_2SO_4$, $NaHSO_3$, $Na_2CO_3$, NaCl, $(NH_4)_2SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, $Cl_2$, NOx, dioxins, and furans, wherein the reactant comprises at least one of $NaHCO_3$, $NaHCO_3 \cdot Na_2CO_3 \cdot 2(H_2O)$, $CaCO_3$, $Ca(OH)_2$, and $Mg(OH)_2$; and filtering the reaction section flue gas in a filtration section to remove NaCl, $Na_2CO_3$, $Na_2SO_4$, $NaNO_3$, $CaCl_2$), $CaSO_4$, $CaCO_3$, $Ca(NO_3)_2$, $MgCl_2$, $MgCO_3$, $MgSO_4$, and $Mg(NO_3)_2$ to form the de-SOx outlet flue gas. NOx can be optionally removed from the de-SOx outlet flue gas in a NOx removal section to form a de-NOx outlet flue gas consisting essentially of at least one of $H_2O$, $CO_2$, $N_2$, $O_2$, dioxins, and furans. Dioxin, furan, or both can be optionally removed from the de-SOx outlet flue gas or the de-NOx outlet flue gas in a dioxin-furan removal section to form a treated outlet flue gas consisting essentially of at least one of $H_2O$, $CO_2$, $N_2$, $O_2$, HCl, and $Cl_2$.

In some embodiments, the thermal oxidizing section comprises an adiabatic thermal oxidizer chamber or a non-adiabatic direct fired boiler.

In some embodiments, removing the dioxin, furan, or both comprises removing the dioxin, furan, or both using a catalyst or by co-injecting activated carbon with dry sorbent.

In some embodiments, the process further comprises: providing the recovered waste heat to at least one piece of equipment in the naphtha complex.

In some embodiments, the NOx removal section and the dioxin-furan removal section are present. In some embodiments, the NOx removal section is present and the dioxin-furan removal section is not present. In some embodiments, the dioxin-furan removal section is present and the NOx removal section is not present. In some embodiments, the NOx removal section and the dioxin-furan removal section are not present.

The naphtha complex can include one of more of the following connected to the thermal oxidation system: an NHT zone, a $C_5$-$C_6$ isomerization zone, a $C_4$ isomerization zone, a reforming zone.

In some embodiments, there is a $C_5$-$C_6$ isomerization zone, and the process further comprises: separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, and HCl and molecules having 4 carbon atoms or less, and a $C_5$-$C_6$ isomerization stabilizer bottoms stream comprising molecules having 4 carbon atoms or more; and thermally oxidizing the NHT stripper off-gas stream, the $C_5$-$C_6$ isomerization stabilizer off-gas stream, or both in the thermal oxidation system.

In some embodiments, there is a $C_5$-$C_6$ isomerization zone and a reforming zone, and the process further comprises: reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; recycling the regenerated reforming catalyst to the catalytic reforming zone; and thermally oxidizing the regenerator off-gas stream in the thermal oxidation system.

In some embodiments, there is a $C_5$-$C_6$ isomerization zone, a reforming zone, and a $C_4$ isomerization zone, and the process further comprises: isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system.

In some embodiments, there is $C_5$-$C_6$, isomerization zone, a reforming zone, and a $C_4$ isomerization zone, and an NHT zone, and the process further comprises: before separating the naphtha stream in the NHT stripper column: hydrotreating a naphtha feed stream comprising molecules having 5 to 12 carbon atoms in a naphtha hydrotreating zone to form a hydrotreated naphtha stream; separating the NHT sour water stream comprising $H_2$, $NH_3$ and $H_2S$ from the hydrotreated naphtha stream in the NHT product separator to form a dewatered hydrotreated naphtha stream, and wherein the dewatered hydrotreated naphtha stream comprises the naphtha stream; and thermally oxidizing the NHT sour water stream in the thermal oxidation system.

In some embodiments, there is a reforming zone, and the process further comprises: reforming a naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system.

In some embodiments, there is a reforming zone and $C_4$ isomerization zone, and the process further comprises: isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system.

In some embodiments, there is a $C_4$ isomerization zone, and the process further comprises: isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system.

In some embodiments, there is a $C_4$ isomerization zone, an NHT zone, and a $C_5$-$C_6$ isomerization zone, and the process further comprises: hydrotreating a naphtha feed stream comprising molecules having 5 to 12 carbon atoms in a naphtha hydrotreating zone to form a hydrotreated naphtha stream; separating the NHT sour water stream comprising $H_2$, $NH_3$, and $H_2S$ from the hydrotreated naphtha stream in the NHT product separator to form a dewatered hydrotreated naphtha stream, and wherein the dewatered hydrotreated naphtha stream comprises the naphtha stream; separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, HCl, and molecules having 4 carbon atoms or less, and a $C_5$-$C_6$ isomerization stabilizer bottoms stream comprising molecules having 4 carbon atoms or more; and thermally oxidizing at least one of the NHT stripper off-gas stream, the $C_5$-$C_6$ isomerization stabilizer off-gas stream, and the NHT sour water stream in the thermal oxidation system.

In some embodiments, there is a NHT zone, and the process further comprises: hydrotreating a naphtha feed stream comprising molecules having 5 to 12 carbon atoms in a naphtha hydrotreating zone to form a hydrotreated naphtha stream; separating the NHT sour water stream comprising $H_2$, HN3 and $H_2S$ from the hydrotreated naphtha stream in the NHT product separator to form a naphtha stream; and thermally oxidizing the NHT sour water stream in the thermal oxidation system.

In some embodiments, there is an NHT zone and a $C_5$-$C_6$ isomerization zone, and the process of claim 17 further comprises: separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, HCl, and molecules having 4 carbon atoms or less, and a $C_5$-$C_6$ isomerization stabilizer bottoms stream comprising molecules having 4 carbon atoms or more; and thermally oxidizing the NHT stripper off-gas stream, the $C_5$-$C_6$ isomerization stabilizer off-gas stream, or both in the thermal oxidation system.

In some embodiments, there is an NHT zone, a $C_5$-$C_6$ isomerization zone, and a reforming zone, and the process further comprises: reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system.

In some embodiments, there is an NHT zone and a reforming zone, and the process further comprises: separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the NHT stripper off-gas stream, the regenerator off-gas stream, or both in the thermal oxidation system.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as metals, and sulfur and nitrogen compounds. The stream can also include aromatic and non-aromatic hydrocarbons. Moreover, the hydrocarbon molecules may be abbreviated $C_1$, $C_2$, $C_3$ . . . $C_n$ where "n" represents the number of carbon atoms in the one or more hydrocarbon molecules. Furthermore, a superscript "+" or "−" may be used with an abbreviated one or more hydrocarbons notation, e.g., $C_3+$ or $C_3-$, which is inclusive of the abbreviated one or more hydrocarbons. As an example, the abbreviation "$C_3+$" means one or more hydrocarbon molecules of three and/or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

FIG. 1 illustrates an example of a typical naphtha complex 100. The process starts with a naphtha feed stream 105. Naphtha feedstocks comprise paraffins, naphthenes, and aromatics, and may comprise small amounts of olefins, boiling within the gasoline range. Feedstocks which may be utilized include straight-run naphthas, catalytically cracked gasoline, partially reformed naphthas or raffinates from extraction of aromatics. The feedstock typically comprises molecules having predominantly 5 to 12 carbon atoms, with a small amount (e.g., less than about 1 mol %) of molecules having 4 carbon atoms and less or having 13 carbon atoms and more. The feedstock is generally encompassed by the range of a full-range naphtha, having an initial boiling point of 30° C. to 35° C., and a final boiling point up to 210° C. (ASTM D86).

The naphtha feed stream 105 is sent to a naphtha hydrotreater (NHT) reaction section 110 (which may include a feed preparation section). In the hydrotreating process, hydrogen gas is contacted with a hydrocarbon stream in the presence of suitable catalysts which are primarily active for the removal of heteroatoms, such as sulfur, nitrogen, and metals from the hydrocarbon feedstock. In hydrotreating, hydrocarbons with double and triple bonds may be saturated. Aromatics may also be saturated. Typical naphtha hydrotreating reaction conditions include a temperature of about 290° C. (550° F.) to about 343° C. (650° F.), a pressure of about 2.4 MPa (350 psig) to about 5.2 MPa (750 psig), a liquid hourly space velocity of about 8 $hr^{-1}$, and a hydrogen rate of about 59 to about 168 $Nm^3/m^3$ oil (350-1,000 scf/bbl). Typical hydrotreating catalysts include at least one Group 8 metal, preferably iron, cobalt and nickel, and at least one Group 6 metal, preferably molybdenum and tungsten, on a high surface area support material, preferably alumina. Other typical hydrotreating catalysts include zeolitic catalysts, as well as noble metal catalysts where the noble metal is selected from palladium and platinum.

The hydrotreated naphtha stream 111 is separated in a NHT product separator 112 into a dewatered hydrotreated naphtha feed stream 115 and a NHT sour water stream 345 comprising $H_2O$, $NH_3$ and $H_2S$. The NHT sour water stream 345 is sent to sour water stripping unit 350 for treatment and removal of the $NH_3$ and $H_2S$ to form stripped sour water stream 355 that is sent for further water treatment or re-used as wash water within the refinery.

The dewatered hydrotreated naphtha feed stream 115 is the naphtha stream sent to the NHT stripper column 120 where it is separated into a NHT stripper off-gas stream 125 and a NHT stripper bottoms stream 130.

The NHT stripper off-gas stream 125 comprises one or more of $H_2$, $H_2S$, NH3 and molecules having 5 carbon atoms or less. The NHT stripper off-gas stream 125 is sent to an NHT stripper off-gas treating unit 135 to remove sulfur. The NHT stripper off-gas treating unit 135 could be an amine contactor, an amine contactor with a regeneration unit, or a scrubbing unit, such as a caustic scrubbing unit, for example.

The sweetened gas (i.e., a gas free of hydrogen sulfide and carbon dioxide) 140 is typically sent to the refinery fuel gas system. The acid gas stream 145 containing the sulfur compounds (e.g., the acid gas stream may comprise $H_2S$, $H_2O$, $CO_2$, and trace amounts of hydrocarbons, such as $C_1$-$C_3$) is sent to a NHT stripper off-gas sulfur treatment unit 150 to remove sulfur compounds. The NHT stripper off-gas sulfur treatment unit 150 could be a sulfur recovery unit, e.g., one based on the Claus process, or a thermal oxidizer with a caustic scrubber, for example.

The off-gas 155 from the NHT stripper off-gas sulfur treatment unit 150 is sent to the tail gas treating unit (not shown). When the NHT stripper off-gas sulfur treatment unit 150 is based on the Claus process, the off-gas 155 includes $H_2S$, $H_2$, CO, $CO_2$, $N_2$, $O_2$, $SO_2$, $SO_3$, $CS_2$, COS, S6, and S8. In this case, the off-gas 155 would be sent to a thermal oxidizer. There may also be a caustic scrubber as well in some cases. When the NHT stripper off-gas sulfur treatment unit 150 is a thermal oxidizer and a caustic scrubber, the off-gas 155, which would primarily be $H_2O$, $CO_2$, $N_2$, $O_2$, can be emitted directly to the atmosphere.

The NHT stripper bottoms stream 130 comprises molecules having five carbon atoms or more. It is sent to the naphtha splitter column 160 where it is separated into a naphtha splitter overhead stream 165 and a naphtha splitter bottoms stream 170.

The naphtha splitter overhead stream 165 comprises molecules having 5-6 carbon atoms. It may be sent to an optional de-isopentanizer column 175 where it is separated into a de-isopentanizer overhead stream 180 and a de-isopentanizer bottoms stream 185.

The de-isopentanizer overhead stream 180 comprises molecules having 5 carbon atoms or less. It is sent to gasoline storage tank (not shown) for blending with other gasoline blending components.

The de-isopentanizer bottoms stream 185 comprises molecules having 5-12 carbon atoms. It is sent to the $C_5$-$C_6$ isomerization zone 190.

Alternatively, the naphtha splitter overhead stream 165 can be sent to the $C_5$-$C_6$ isomerization zone 190.

The $C_5$-$C_6$ isomerization zone 190 can be any type of isomerization zone that takes a stream of $C_5$-$C_6$ straight-chain hydrocarbons or a mixture of straight-chain, branched-chain, and cyclic hydrocarbons and converts straight-chain hydrocarbons in the feed mixture to branched-chain hydrocarbons and branched hydrocarbons to more highly branched hydrocarbons, thereby producing an effluent having branched-chain and straight-chain hydrocarbons. In some embodiments, the isomerization zone can include one or more reactors.

The de-isopentanizer bottoms stream 185 (or the naphtha splitter overhead stream 165) and hydrogen are contacted in the $C_5$-$C_6$ isomerization zone 190 with an isomerization catalyst forming $C_5$-$C_6$ isomerization outlet stream 195. The catalyst composites that can be used in the $C_5$-$C_6$ isomerization zone 190 include traditional isomerization catalysts including chloride platinum alumina, crystalline aluminosilicates or zeolites, and other solid strong acid catalysts such as sulfated zirconia and modified sulfated zirconia. Suitable catalyst compositions of this type will exhibit selective and substantial isomerization activity under the operating conditions of the process.

Operating conditions within the $C_5$-$C_6$ isomerization zone 190 are selected to maximize the production of isoalkane product from the feed components. Temperatures within the isomerization zone will usually range from about 400 to about 235° C. (1000 to 455° F.). Lower reaction temperatures usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes, temperatures in the range of from about 600 to about 160° C. are suitable. The isomerization zone may be maintained over a wide range of pressures. Pressure conditions in the isomerization of $C_4$-$C_6$ paraffins range from about 600 KPa(g) to about 6900 KPa(g). In other embodiments, pressures for this process are in the range of from about 2000 kPa(g) to 5000 kPa(g). The feed rate to the reaction zone can also vary over a wide range. These conditions include liquid hourly space velocities ranging from about 0.5 to about 12 $hr^{-1}$ however, with some embodiments having space velocities between about 1 and about 6 $hr^{-1}$.

The $C_5$-$C_6$ isomerization outlet stream 195 is sent to the $C_5$-$C_6$ isomerization stabilizer column 200 where it is separated into $C_5$-$C_6$ isomerization stabilizer off-gas stream 205, and $C_5$-$C_6$ isomerization stabilizer bottoms stream 210.

The $C_5$-$C_6$ isomerization stabilizer off-gas stream 205 comprises $H_2$, HCl, and molecules having 4 carbon atoms or less. It is sent to a $C_5$-$C_6$ off-gas chloride treatment unit 215 to remove chloride. The $C_5$-$C_6$ off-gas chloride treatment unit 215 could be an off-gas scrubber or other chloride treating unit, such as the ReChlor™ process unit available from UOP LLC. The ReChlor™ process is a process for removing chorine-containing species from a hydrocarbon containing vapor stream by contacting the vapor stream with a fluid hydrocarbon sorbent at conditions effective for sorption of the chorine-containing species with the fluid hydrocarbon sorbent.

The off-gas 220 from the $C_5$-$C_6$ off-gas chloride treatment unit 215 (which comprises molecules having 4 carbon atoms or less) is sent to the refinery gas fractionation zone.

The $C_5$-$C_6$ isomerization stabilizer bottoms stream 210 comprises hydrocarbons having 4 carbon atoms or more. It is sent to the de-isohexanizer column 225 where it is separated into a de-isohexanizer overhead stream 230, de-isohexanizer side cut stream 235, and a deisohexanizer bottoms stream 240.

The de-isohexanizer overhead stream 230 comprises molecules having 6 carbon atoms or less. It is sent to the gasoline storage tank (not shown) for blending with other gasoline blending components.

The de-isohexanizer side cut stream 210 comprises methylpentane and n-hexane. It is recycled to the $C_5$-$C_6$ isomerization zone 190.

The deisohexanizer bottoms stream 240 comprises molecules having 6 carbon atoms or more. It is sent to the gasoline storage tank for blending with other gasoline blending components.

The naphtha splitter bottoms stream 170 comprises molecules having 6-12 carbon atoms. It is sent to the catalytic reforming zone 245. In a common form, the reforming process can employ the catalyst particles in several reaction zones interconnected in a series flow arrangement. There may be any number of reaction zones, but usually the number of reaction zones is 3, 4 or 5. Because reforming reactions occur generally at an elevated temperature and are generally endothermic, each reaction zone usually has associated with it one or more heating zones, which heat the reactants to the desired reaction temperature.

The catalyst particles are typically comprised of one or more Group VIII (IUPAC 8-10) noble metals (e.g., platinum, iridium, rhodium, and palladium) and a halogen combined with a porous carrier, such as a refractory inorganic oxide. Typical feed inlet temperature for the reformers are between 480 and 580° C. (824 and 1076° F.). The reformers may have different operating temperatures, for example, with a first reforming reactor having a temperature between 500 to 540° C. (932 to 1004° F.) and a second, subsequent reforming reactor having a temperature greater than 540° C. (1004° F.). The reformers can be operated at a range of pressures generally from atmospheric pressure of about 0 to about 6,895 kPa(g) (about 0 psi(g) to about 1,000 psi(g)). The reaction conditions also include a liquid hour space velocity (LHSV) in the range from 0.6 $hr^{-1}$ to 10 $hr^{-1}$. Shorter residence time is desirable when utilizing the higher temperatures. The catalyst also has a residence time in the reformers of between 0.5 hours and 36 hours.

The reformer effluent 250 comprises a mixture of paraffin, naphthene, and aromatic molecules having 5 carbon atoms or more. It is sent to the gasoline storage tank (not shown) for either use as a high-octane blend stock for making gasoline or as a source of aromatics for the petrochemicals industry.

Spent reforming catalyst 255 is sent to the continuous catalyst regenerator zone 260. Over time, coke accumulates on the catalytic reforming catalyst. Carbon is burned off the spent (partially deactivated) catalyst in the continuous catalyst regenerator zone 260. The regenerated catalyst 265 is returned to the catalytic reforming zone 245.

The regenerator off-gas stream 270 comprises one or more of $N_2$, $H_2O$, $CO_2$, HCl, $O_2$, and $Cl_2$. It is sent to the regenerator off-gas chloride treatment unit 275 to remove chloride species. The regenerator off-gas chloride treatment unit 275 could be an off-gas scrubber or other chloride treatment process, such as the Chlorsorb™ process from UOP LLC. The Chlorsorb™ process is a process for recovering a chlorine-containing species from a hydrocarbon conversion process gas stream by contacting the gas stream with an aluminum-containing solid sorbent under conditions effective to adsorb the chorine-containing species with the solid sorbent.

In some cases, the vent gas 280 from the regenerator off-gas chloride treatment unit 275 is sent to the regenerator off-gas dioxin-furan removal unit 285 where dioxin and/or furan is removed from the vent gas 280. The treated gas 290, which contains one or more of $N_2$, $H_2O$, $CO_2$, HCl, $O_2$, and $Cl_2$. is vented to the atmosphere.

In some naphtha complexes, there is a $C_4$ isomerization unit 295. A $C_4$ feed stream 300 comprises molecules having 4 carbon atoms. It is sent to the $C_4$ isomerization zone 305 where n-butane is converted to iso-butane. The reaction conditions for the $C_4$ isomerization unit 295 typically include temperatures in the range of 93° F. to 204° C. (200° F. to 400° F.), pressures in the range of 1.5-2.0 MPa, a LHSV of about 2 $hr^{-1}$ and an $H_2$/HC mole ratio of 0.5-2.

The $C_4$ isomerization outlet stream 310 is sent to $C_4$ isomerization stabilizer column 315 where it is separated into $C_4$ isomerization stabilizer off-gas stream 320, and $C_4$ isomerization stabilizer bottoms stream 325.

The $C_4$ isomerization stabilizer off-gas stream 320 comprises hydrogen, nitrogen, HCl, and molecules having 4 carbon atoms or less. It is sent to a $C_4$ off-gas chloride treatment unit 330 to remove chloride. The $C_4$ off-gas chloride treatment unit 330 could be an off-gas scrubber, for example.

The off-gas 335 from the $C_4$ off-gas chloride treatment unit 330 (which comprises molecules having 4 carbon atoms or less, i.e., a gas free of chloride-containing species) is sent to refinery gas fractionation zone. The spent caustic 340 from the $C_4$ scrubber unit 330 (which comprises mainly $H_2O$, NaHS, and $Na_2S$) is sent to refinery spent caustic system.

The $C_4$ isomerization stabilizer bottoms stream 325 comprises molecules having 4 carbon atoms or more. It can be blended directly into gasoline or sent to an alkylation unit.

Figure 2:
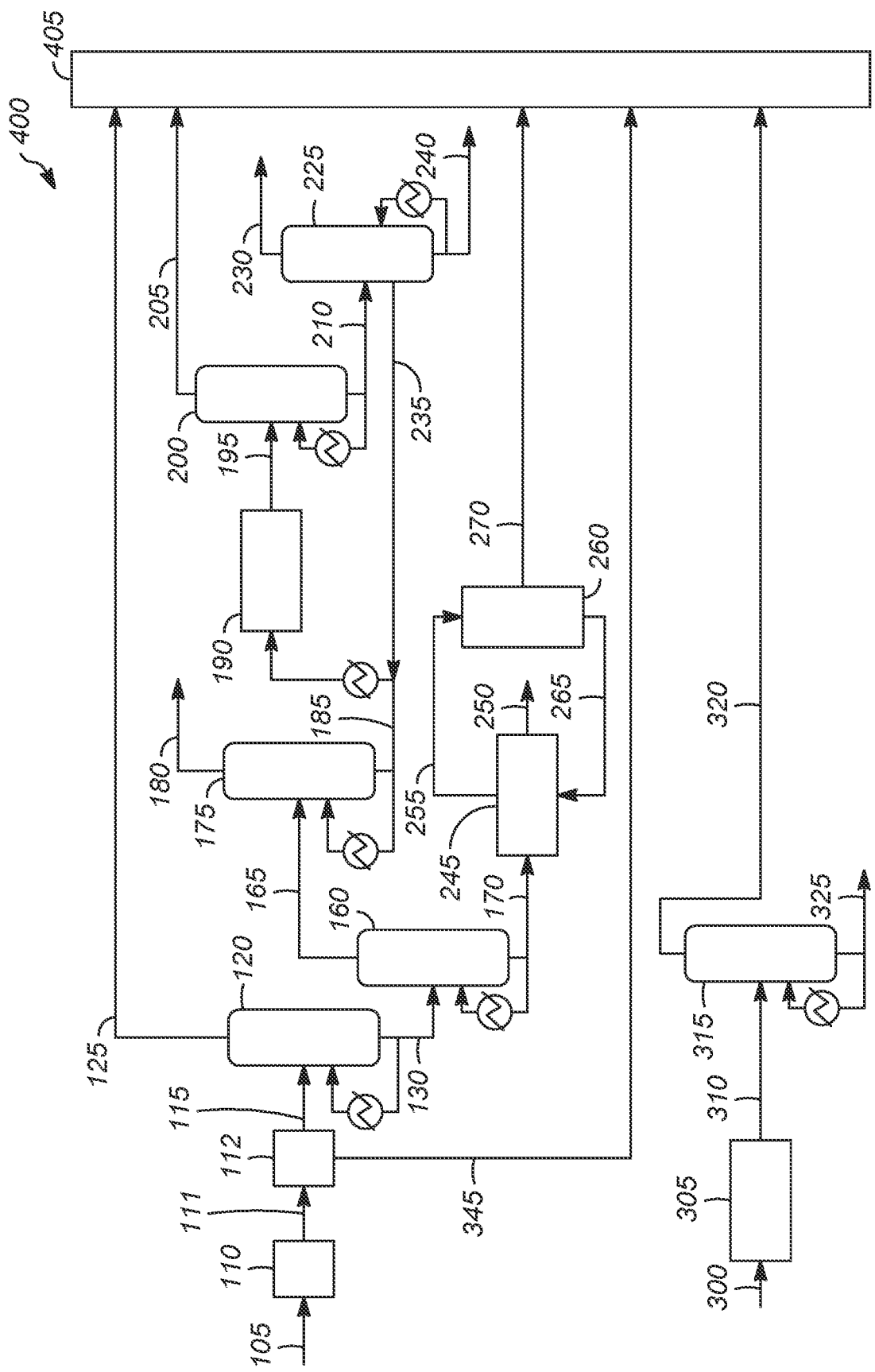
FIG. 2 is an illustration of one embodiment of a naphtha complex according to the present invention.

FIG. 2 illustrates an example of a naphtha complex 400 embodying the claimed process.

The various parts of the naphtha complex, including the NHT reactor section 110, NHT product separator 112, the NHT stripper column 120, the naphtha splitter column 160, the de-isopentanizer column 175 (if present), the $C_5$-$C_6$ isomerization zone 190, the $C_5$-$C_6$ isomerization stabilizer column 200, the de-isohexanizer column 225, the catalytic reforming zone 245, the continuous catalyst regenerator zone 260, the $C_4$ isomerization zone 305, and the $C_4$ isomerization stabilizer column 315, are as described above.

However, in this embodiment, at least one of the NHT stripper off-gas stream 125, the $C_5$-$C_6$ isomerization stabilizer off-gas stream 205, the regenerator off-gas stream 270, the $C_4$ isomerization stabilizer off-gas stream 320, and the NHT sour water stream 345 are thermally oxidized in a thermal oxidation system 405.

Depending on the process units in the naphtha complex, this allows one or more of the following process units to be eliminated: the NHT stripper off-gas treating unit 135, the NHT stripper off-gas sulfur treatment unit 150, the $C_5$-$C_6$ off-gas chloride treatment unit 215, the regenerator off-gas chloride treatment unit 275, the regenerator off-gas dioxin-furan removal unit 285, the $C_4$ off-gas chloride treatment unit 330, and the sour water stripping unit 350. The reduction in process units may result in significantly lower capital and operating costs.

Figure 3:
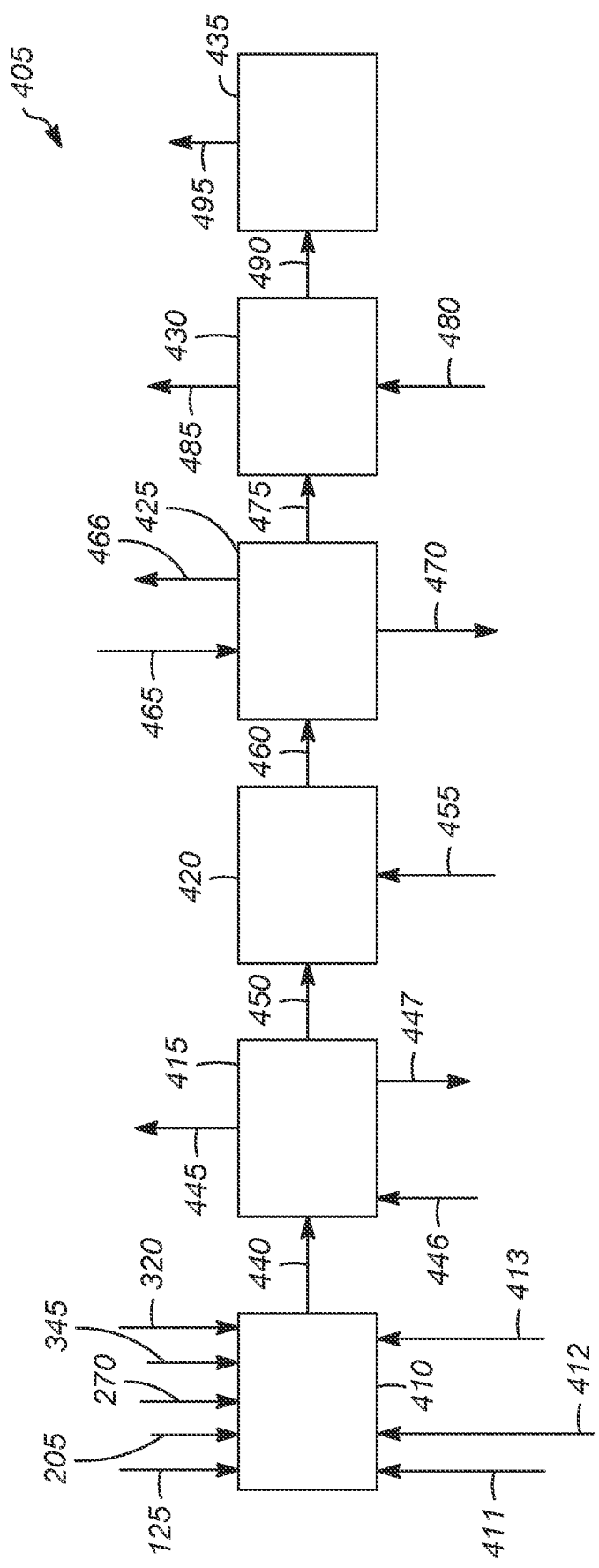
FIG. 3 is an illustration of one embodiment of a thermal oxidation system according to the present invention.

One embodiment of a thermal oxidation system 405 is illustrated in FIG. 3. The thermal oxidation system 405 comprises a thermal oxidizing section 410, an optional waste heat recovery section 415, a quench section 420, a scrubbing section 425, an optional NOx removal 430, and an optional dioxin-furan removal section 435.

At least one of the NHT stripper off-gas stream 125, the $C_5$-$C_6$ isomerization stabilizer off-gas stream 205, the regenerator off-gas stream 270, the $C_4$ isomerization stabilizer off-gas stream 320, and the NHT sour water stream 345, along with a combustion air stream 411, make-up natural gas or fuel gas stream 412 (as needed), and quench stream 413 (as needed) are introduced into the thermal oxidizing section 410. The inlet temperature of the thermal oxidizing section 410 is typically in the range of −30-500° C. with a pressure of −1 kPa(g) to 3000 kPa(g). The outlet temperature is typically in the range of 650-1300° C. with a pressure of −1 kPa(g) to 50 kPa(g). The residence time in the thermal oxidizing section 410 is between 0.5 and 2 seconds. When a direct fired boiler is used, the temperature may be much higher, for example, 2100° C. Any suitable thermal oxidizing section 410 could be used, including, but not limited to, an adiabatic thermal oxidizer chamber or a non-adiabatic direct fired boiler. The thermal oxidizing section 410 can be forced draft, induced draft, or a combination of both. An optional selective non-catalytic reduction (SNCR) section may be present in some cases. The inlet temperature of the SNCR section is typically in the range of 650-1300° C. (2100° C. with a direct fired boiler) with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel. The hydrocarbons are converted to $H_2O$ and $CO_2$. The sulfides from the sulfur species (e.g., $H_2S$) present in feed are converted to oxidized sulfur particulate SOx including, but not limited to, $SO_2$ and $SO_3$, and $H_2O$. The nitrogen from the nitrogen bound molecules (e.g. $NH_3$) present in the feed are converted to Nitrogen ($N_2$) and NOx, including but not limited to NO, $NO_2$. The HCl and $Cl_2$ (if any) remain.

The flue gas stream 440 from the thermal oxidizing section 410 consists essentially of one or more of $H_2O$, $CO_2$, $N_2$, $O_2$, SOx (i.e., $SO_2$ and $SO_3$), NOx (i.e., NO and $NO_2$), HCl, $Cl_2$, dioxins, and furans. "Consisting essentially of" means that one of more of the gases or vapors are present and there are no other gases or vapors present which require treatment before being released to the atmosphere, The flue gas stream 440 is sent to the optional waste heat recovery section 415. The inlet temperature of the optional waste heat recovery section 415 is typically in the range of 650-1300° C. with a pressure of −2 kPa(g) to 50 kPa(g). The outlet temperature is typically in the range of 200-400° C. with a pressure of −2 kPa(g) to 50 kPa(g). Suitable waste heat recovery apparatus and methods include, but are not limited to, a waste heat recovery boiler, including, but not limited to, a firetube boiler or a watertube boiler. Boiler feed water or oil stream 446 enters the waste heat recovery section 415 where a portion is converted to steam or hot oil stream 445, with the remainder exiting as blowdown water or oil stream 447. In some cases, the steam can be converted to electricity, for example using a steam turbine, if desired.

The recovered waste heat in steam or hot oil stream 445 can be in the form of low (e.g., less than 350 kPa(g)), medium (e.g., 350 kPa(g) to 1750 kPa(g)), or high (e.g., greater than 1750 kPa(g)) pressure saturated or superheated steam, hot oil, and/or electricity. The recovered heat can be used to provide heat to one or more pieces of equipment or process streams in the naphtha complex or to other parts of the plant. For example, the recovered waste heat in steam or hot oil steam stream 445 can be used to preheat gas in the catalytic reforming zone 245, in the reboilers of various columns in the naphtha complex or other areas of the plant, or for other heat requirements.

The flue gas stream 450 from the optional waste heat recovery section 415 flows to the quench section 420 where the temperature of the flue gas is reduced to the saturation temperature using quench stream 455. The inlet temperature of the quench section 420 is typically in the range of 200-400° C. with a pressure of −3 kPa(g) to 50 kPa(g). The inlet temperature could be up to 1300° C. if no waste heat reboiler is present. The outlet temperature is typically in the range of 45-150° C. with a pressure of −3 kPa(g) to 50 kPa(g). Quench stream 455 includes, but is not limited to, water, air, recycle flue gas, or combinations thereof.

The quenched flue gas stream 460 from the quench section 420 is sent to the SOx removal section 425 for removal of at least one of the SOx, HCl and $Cl_2$. The inlet temperature of the SOx removal section 425 is typically in the range of 45-150° C. with a pressure of −4 kPa(g) to 50 kPa(g). The outlet temperature is typically in the range of 45-150° C. with a pressure of −4 kPa(g) to 50 kPa(g). For example, the SOx removal section may be a scrubbing section in which a caustic stream 465 comprising aqueous NaOH is introduced into the scrubbing section where it reacts with the at least one of SOx, HCl, and $Cl_2$ in the flue gas. An aqueous stream 470 containing aqueous $Na_2SO_3$, $Na_2SO_4$, and NaCl exits the scrubbing section 425. If desired, a reducing agent such as $NaHSO_4$ or $H_2O_2$, can be included to react with the $Cl_2$ to form HCl which reacts to form NaCl. Alternatively, stream 465 could be an $NH_3$ based solution. The $NH_3$ reacts with the SOx to form $(NH_4)_2SO_4$. The $NH_3$ reacts with the $Cl_2$ to form $N_2$ and HCl, followed by the reaction of the HCl with the $NH_3$ forming $NH_4Cl$. A separate reducing agent is not needed when $NH_3$ is used. In this case, the aqueous stream 470 would include $H_2O$, NaCl, $(NH_4)_2SO_4$ and $NH_4Cl$.

The de-SOx outlet flue gas stream 475 from the scrubbing section 425 has a reduced level of SOx compared to the incoming quenched flue gas stream 460. The de-SOx outlet flue gas stream 475 comprises one or more of $H_2O$, $CO_2$, $N_2$, $O_2$, NOx, dioxins, and furans.

If NOx is present in the de-SOx outlet flue gas stream 475, the de-SOx outlet flue gas stream 475 is sent to the optional NOx removal section 430 to remove NOx. The inlet temperature of the NOx removal section 430 is typically in the range of 150-300° C. with a pressure of −5 kPa(g) to 50 kPa(g). The outlet temperature is typically in the range of 200-350° C. with a pressure of −5 kPa(g) to 50 kPa(g). The de-SOx outlet flue gas stream 475 may need to be heated to obtain the desired inlet temperature for the NOx removal section 430. For example, the NOx removal section 430 can be a selective catalytic reduction (SCR) section in which an ammonia and/or urea stream 480 are introduced into the SCR section 430 where it reacts with the NOx and forms $N_2$ and $H_2O$. Any suitable SCR catalyst could be used, including but not limited to, ceramic carrier materials such as titanium oxide with active catalytic components such as oxides of base metals including $TiO_2$, $WO_3$ and $V_2O_5$, or an activated carbon based catalyst. The de-NOx outlet flue gas stream 490 comprises one or more of $H_2O$, $CO_2$, $N_2$, $O_2$, dioxins, and furans.

If there are any halogens present in the feed, this may result in the formation of dioxin and/or furans. These compounds must be removed before the gases can be vented to the atmosphere. If dioxins and/or furans are present in the de-SOx outlet flue gas stream 475 or the de-NOx outlet flue gas 490, the de-SOx outlet flue gas stream 475 or the de-NOx outlet flue gas stream 490 is sent to the optional dioxin-furan removal section 435 for removal of the dioxin and/or furan. The dioxin and furans can be removed using a catalyst. The inlet temperature of the dioxin-furan removal section 435 is typically in the range of 150-250° C. with a pressure of −6 kPa(g) to 50 kPa(g). The outlet temperature is typically in the range of 150-250° C. with a pressure of −6 kPa(g) to 50 kPa(g). The treated outlet flue gas stream 495, consisting essentially of one or more of $H_2O$, $CO_2$, $N_2$, $O_2$, HCl, and $Cl_2$, can be vented to the atmosphere.

If there levels of NOx and dioxins and/or furans in the de-SOx outlet flue gas stream 475 exceed environmental regulations, the system will probably contain both the NOx removal section 430 and dioxin-furan removal section 435. In this case, deSOx outlet flue gas stream 475 will have a slightly higher temperature than de-NOx outlet flue gas stream 490. There may be a need for quenching the de-NOx outlet flue gas stream 490 before it enters the dioxin-furan removal section 430.

If the de-SOx outlet flue gas stream 475 does not contain NOx, dioxin, or furans, the optional NOx removal section 430 and optional dioxin-furan removal section 435 are not present. The de-SOX outlet flue gas stream 466, consisting essentially of one or more of $H_2O$, $CO_2$, $N_2$, and $O_2$, can be vented to the atmosphere.

If the de-SOx outlet flue gas stream 475 contains NOx, but no dioxin or furans, the optional dioxin-furan removal section 435 is not present. The de-NOx outlet flue gas stream 485, consisting essentially of one or more of $H_2O$, $CO_2$, $N_2$, and $O_2$, can be vented to the atmosphere.

If the de-SOx outlet flue gas stream 475 contains dioxin or furans, but not NOx, the optional NOx removal section 430 is not present. The de-SOx outlet flue gas stream 475 is sent to the optional dioxin-furan removal section 435. The treated outlet flue gas stream 495, consisting essentially of one or more of $H_2O$, $CO_2$, $N_2$, $O_2$, HCl, and $Cl_2$, can be vented to the atmosphere.

Figure 4:
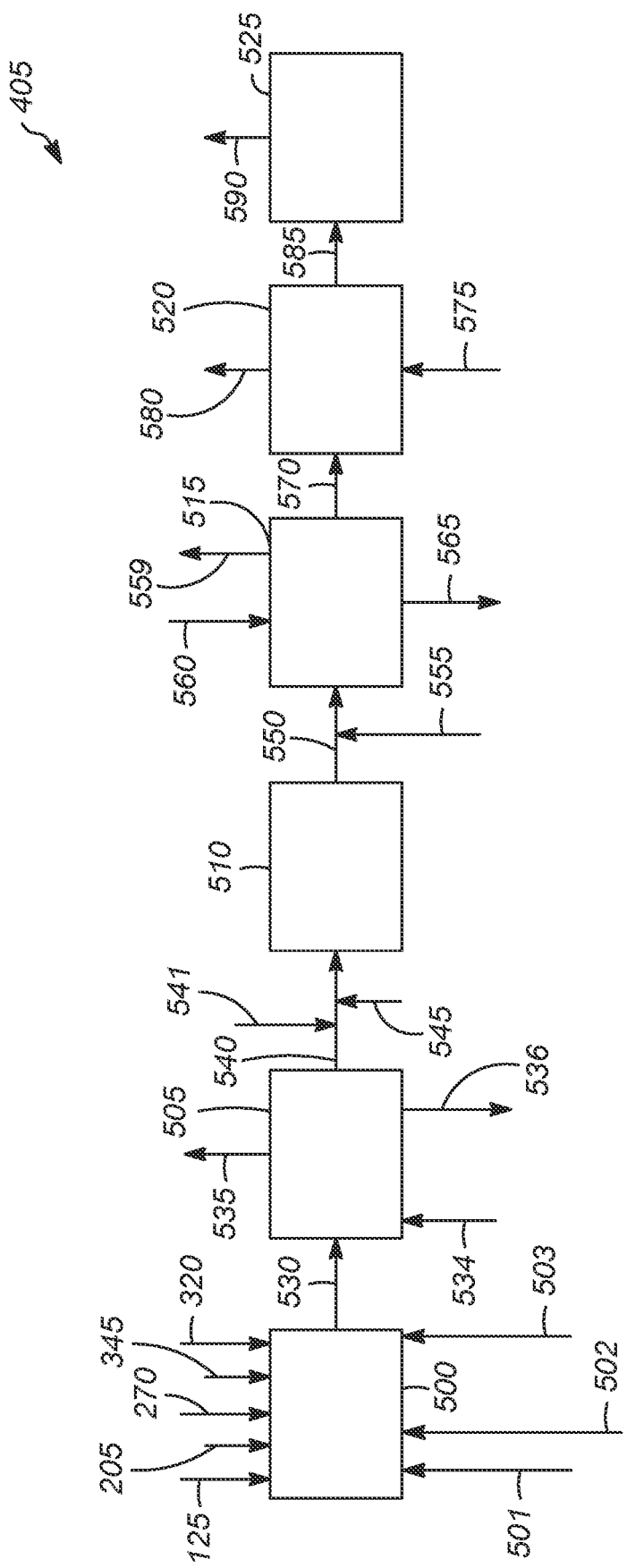
FIG. 4 is an illustration of another embodiment of a thermal oxidation system according to the present invention.

Another embodiment of the thermal oxidation system 405 is illustrated in FIG. 4. The thermal oxidation system 405 comprises a thermal oxidizing section 500, an optional waste heat recovery section 505, a SOx removal section 510, a filtration section 515, an optional NOx removal section 520, and an optional dioxin-furan removal section 525.

At least one of the NHT stripper off-gas stream 125, the $C_5$-$C_6$ isomerization stabilizer off-gas stream 205, the regenerator off-gas stream 270, the $C_4$ isomerization stabilizer off-gas stream 320, and the NHT sour water stream 345 are introduced into the thermal oxidizing section 500, as described above. In some cases, one or more of a combustion air stream 501, make-up natural gas stream 502, and quench stream 503 are also introduced into the thermal oxidizing section 410.

The inlet temperature of the thermal oxidizing section 500 is typically in the range of −30-500° C. with a pressure of −1 kPa(g) to 3000 kPa(g). The outlet temperature is typically in the range of 650-1300° C. (2100° C. with a direct fired boiler) with a pressure of −1 kPa(g) to 50 kPa(g). The residence time in the thermal oxidizing section 500 is between 0.5 and 2 seconds. Any suitable thermal oxidizing section 500 could be used, including, but not limited to, an adiabatic thermal oxidizer chamber or a non-adiabatic direct fired boiler. The thermal oxidizing section 500 can be forced draft, induced draft, or a combination of both. The inlet temperature of the optional SNCR section is typically in the range of 650-1300° C. (2100° C. with a direct fired boiler) with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel.

The flue gas stream 530 from the thermal oxidizing section 500 comprises one or more of $H_2O$, $CO_2$, $N_2$, $O_2$, SOx, NOx, HCl, $Cl_2$, dioxins, and furans. The flue gas stream 530 is sent to the optional waste heat recovery section 505. Boiler feed water or oil stream 534 enters the optional waste heat recovery section 505 where a portion is converted to steam or hot oil stream 535, with the remainder exiting as blowdown water or oil 536. The inlet temperature of the optional waste heat recovery section 505 is typically in the range of 650-1300° C. with a pressure of −2 kPa(g) to 50 kPa(g). The outlet temperature is typically in the range of 200-400° C. with a pressure of −2 kPa(g) to 50 kPa(g). Suitable waste heat recovery apparatus and methods are described above. The recovered waste heat in steam or hot oil stream 535 can be in the form of low, medium, or high pressure saturated or superheated steam, hot oil, and/or electricity. The recovered waste heat in steam or hot oil stream 535 can be used to preheat gas in the catalytic reforming zone 245, in the reboilers of various columns in the naphtha complex, or elsewhere in the plant, or for other heat requirements.

The flue gas stream 540 from the optional waste heat recovery section 505 is sent to the SOx removal section 510 to convert at least one of SOx, HCl, and $Cl_2$. The inlet temperature of the SOx removal section 510 is typically in the range of 200-400° C. with a pressure of −3 kPa(g) to 50 kPa(g). The outlet temperature is typically in the range of 200-400° C. with a pressure of −3 kPa(g) to 50 kPa(g). Fresh sorbent 541 and optionally recycled sorbent 545, (comprising a mixture of one or more NaCl, $Na_2CO_3$, $Na_2SO_4$, $CaCl_2$, $CaSO_4$, $CaCO_3$, $MgCl_2$, $MgCO_3$, $MgSO_4$, and $MgCO_3$, depending on the compounds used in the reactant used, as discussed below) can be added to the flue gas stream 540. For example, the SOx removal section 510 may contain a reactant, such as $NaHCO_3$, $NaHCO_3.Na_2CO_3.2(H_2O)$, $CaCO_3$, $Ca(OH)_2$, and $Mg(OH)_2$, which reacts with the SOx, NOx and HCl to form NaCl, $Na_2CO_3$, $Na_2SO_4$, $NaNO_3$, $CaCl_2$, $CaSO_4$, $CaCO_3$, $MgCl_2$, $MgCO_3$, $MgSO_4$ and $Mg(NO_3)_2$, dioxins and furans. The reaction section flue gas stream 550 has a less HCl, SOx, and NOx compared to the incoming flue gas stream 540. The reaction section flue gas stream 550 comprises one or more of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, $Cl_2$, NOx, dioxins, and furans.

The de-SOx outlet flue gas stream 550 is combined with a quench stream 555 comprising air, and/or water, and/or quenched flue gas. The temperature of the de-SOx outlet flue gas stream 510 is typically reduced from 200-400° C. with a pressure of −4 kPa(g) to 50 kPa(g) to 150-250° C. with a pressure of −4 kPa(g) to 50 kPa(g). The quenched de-SOx outlet flue gas stream 550 is sent to the filtration section 515 for removal of the $Na_2CO_3$, $Na_2SO_4$, NaCl, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$.

The inlet temperature of the filtration section 515 is typically in the range of 150-350° C. with a pressure of −5 kPa(g) to 50 kPa(g). The outlet temperature is typically in the range of 150-350° C. with a pressure of −5 kPa(g) to 50 kPa(g). The filtration section 515 comprises a bag filter, and/or a ceramic filter, and/or an electrostatic precipitator. An instrument air purge or high voltage DC 560 is introduced into the filtration section 515. In the case of the instrument air purge, it purges the retained material from the filter. In the case of the high voltage stream, it charges the cathodes of the ESP. The particulate is removed from the ESP by vibration. Dry residue stream 565 comprising one or more of NaCl, $Na_2CO_3$, $Na_2SO_4$, $NaNO_3$, $CaCl_2$, $CaSO_4$, $Ca_2CO_3$, $Ca(NO_3)_2$ $MgCl_2$, $MgCO_3$, $MgSO_4$, and $Mg(NO_3)_2$ exits the filtration section 515. The filtered flue gas 570 comprises one or more of $H_2O$, $CO_2$, $N_2$, $O_2$, NOx, dioxins, and furans.

If NOx is present in the filtered flue gas stream 570, the filtered flue gas stream 570 is sent to the optional NOx removal 520 to remove NOx as discussed above. The inlet temperature of the NOx removal section 520 is typically in the range of 150-300° C. with a pressure of −6 kPa(g) to 50 kPa(g). The outlet temperature is typically in the range of 200-350° C. with a pressure of −6 kPa(g) to 50 kPa(g). For example, an ammonia and/or urea stream 575 can be introduced into the optional NOx removal section 520 where it reacts with the NOx and forms $N_2$. The de-NOx outlet flue gas stream 585 consists essentially of one or more of $H_2O$, $CO_2$, $N_2$, $O_2$, dioxins, and furans.

If there are any halogens present in the feed, this may result in the formation of dioxin and/or furans. These compounds must be removed before the gases can be vented to the atmosphere. If dioxins and/or furans are present in the filtered flue gas stream 570 or the de-NOx outlet flue gas stream 585, the filtered flue gas stream 570 or the de-NOx outlet flue gas stream 585 is sent to the optional dioxin-furan removal section 525 for removal of the dioxin and/or furan. The dioxin and furans can be removed using a catalyst, or by co-injecting activated carbon. With the catalyst, the dioxin and furans react the catalyst, such as a catalyst containing e.g., $TiO_2$, $WO_3$ and $V_2O_5$, to form trace amounts of $CO_2$, $H_2O$, HCl, and $Cl_2$. In the case of the activated carbon, it would be co-injected with the dry sorbent 541 upstream of the SOx removal section 510. The dioxins and/or furan would be adsorbed on the carbon, and removed from via dry residue stream 565. The inlet temperature of the dioxin-furan removal section 525 is typically in the range of 150-250° C. with a pressure of −7 kPa(g) to 50 kPa(g). The outlet temperature is typically in the range of 150-250° C. with a pressure of −7 kPa(g) to 50 kPa(g). The treated outlet flue gas stream 590, consisting essentially of one or more of $H_2O$, $CO_2$, $N_2$, $O_2$, HCl, and $CL_2$, can be vented to the atmosphere.

If the filtered flue gas stream 570 does not contain NOx, dioxin, or furans, the optional NOx removal or selective catalytic reduction section 520 and optional dioxin-furan removal section 525 are not present. The filtered flue gas stream 559, consisting essentially of one or more of $H_2O$, $CO_2$, $N_2$, and $O_2$, can be vented to the atmosphere.

If the filtered flue gas stream 570 contains NOx, but no dioxin or furans, the optional dioxin-furan removal section 525 is not present. The de-NOx outlet flue gas stream 580, consisting essentially of one or more of $H_2O$, $CO_2$, $N_2$, and $O_2$, can be vented to the atmosphere.

If the filtered flue gas stream 570 contains dioxin or furans, but not NOx, the optional NOx removal section 520 is not present. The filtered flue gas 570 stream is sent to the optional—dioxin-furan removal section 525. The treated outlet flue gas stream 590, consisting essentially of one or more of $H_2O$, $CO_2$, $N_2$, $O_2$, and traces of HCl, and $Cl_2$, can be vented to the atmosphere.

Example

Table 1 shows a partial heat and mass balance for the naphtha complex of FIGS. 2-3. The streams identified in Table 1 are the following:
Targeted effluents naphtha complex send to TO:
  NHT stripper column off-gas—NHT stripper column off-gas stream 125
  Regenerator off-gas stream—Regenerator off-gas stream 270
  C5/C6 stabilizer off-gas—$C_5$-$C_6$ isomerization stabilizer off-gas stream 205
  C4 isomerization stabilizer off-gas—$C_4$ isomerization stabilizer off-gas stream 320
  NHT sour water—NHT sour water stream 345
TO section streams—Thermal oxidizing section 410 streams:
  Combustion air—combustion air stream 411
  Quench air—quench air stream not 413
  Make-up natural gas—make-up natural gas stream 412
  Fuel gas outlet TO section—flue gas stream 440
WHB section—Waste heat recovery section 415 stream:
  Flue gas outlet WHB section—flue gas stream 450
  BFW in—boiler feed water or oil stream 446
  Steam out—steam or hot oil stream 445
  Condensate—blowdown water or oil stream 447

As Table 1 demonstrates, the thermal oxidation system can be used to treat streams which are normally treated by other treatment units, such as the sour water stripping unit for the NHT sour water, the amine treatment unit or the caustic treatment unit for the NHT stripper off-gas, the caustic scrubber unit or other chloride treatment unit for the off-gas from the $C_5$-$C_6$ isomerization zone and the $C_4$ isomerization zone, and the caustic scrubber unit or other chloride treatment unit for the regenerator off-gas. Furthermore, this example demonstrates that energy can be recovered in the form of steam, which subsequently can be used in the naphtha complex to offset steam requirements from sources outside the battery limit. Given the high efficiency SOx removal, NOx removal, and dioxin-furan destruction sections (not included in Table 1), corrosion of equipment in naphtha complex will be eliminated, as well as environmental concerns pertaining to emissions. (A complete heat and mass balance is not shown given that the thermal oxidizer flue gas treatment is known and proven technology.)

TABLE 1

| Stream names | Targeted effluents naphtha complex sent to TO | | | | | TO section[1] | | | | | WHB section | | |
|---|---|---|---|---|---|---|---|---|---|---|---|---|---|
| | NHT Stripper column off-gas | Regenerator off-gas stream | C5/C6 Stabilizer off-gas | C4 isomerization stabilizer off-gas | NHT Sour Water | Combustion Air | Quench Air | Make-up Natural Gas | Flue gas outlet TO section | Flue gas outlet WHB section | BFW in | Steam out | Condensate |
| Stream Number | 125 | 270 | 205 | 320 | 345 | 411 | 413 | 412 | 440 | 450 | 446 | 445 | 445 |
| Temperature, °C. | 48 | 480 | 38 | 38 | 48 | 30 | 30 | 30 | 1200 | 240 | 15 | 9.69 | 10 |
| Pressure, kg/cm2 (g) (of source vessel) | 10.5 | 2.4 | 14 | 21.8 | 10.5 | 0.1 | 0.1 | 5 | 0.3 | 0.2 | 105 | 184 | 182 |
| Nitrogen | | | | | | 2993.77 | 1119.34 | | | | | | |
| Sulfur oxides (expressed as SO2) | | | | | | | | | 7.52 | 7.52 | | | |
| Nitrogen oxides (expressed as NO2) | | | | | | | | | 0.627 | 0.627 | | | |
| Ammonia | 1.20E−04 | | | | 6.8E−03 | | | | | | | | |
| Water (gas/liquid) | 7.70E−01 | 1.31 | | | 449.59 | 83.13 | 31.08 | | 1104.44 | 1104.44 | 4030.00 | 3951.00 | 79.00 |
| Oxygen | | 2.5E−02 | | | | 793.42 | 296.65 | | 455.34 | 455.34 | | | |
| Nitrogen | | 9.14 | | | | | | | 4122.26 | 4122.26 | | | |
| Carbon dioxide | | 2.00 | | | | | | | 359.96 | 359.96 | | | |
| Hydrogen sulfide | 7.40 | | | | 0.12 | | | | | | | | |
| Chlorine (considered as convert to HCl) | | 1.40E−04 | | | | | | | | | | | |
| Hydrogen chloride | | 2.7E−02 | 0.54 | 0.13 | | | | | 0.70 | 0.70 | | | |
| Hydrogen | 34.66 | | 74.06 | 15.50 | | | | | | | | | |
| Methane | 4.74 | | 5.36 | 1.38 | | | | | | | | | |
| Ethane | 3.66 | | 4.46 | 1.63 | | | | | | | | | |
| Propane | 1.98 | | 12.66 | 3.90 | | | | | | | | | |
| Isobutane | 1.11 | | 28.58 | 5.02 | | | | | | | | | |
| n-butane | 18.05 | | 3.18 | 0.50 | | | | | | | | | |
| Isopentane | 4.22 | | 2.90 | | | | | | | | | | |
| n-pentane | 1.67 | | 1.9E−01 | 4.6E−04 | | | | | | | | | |
| Cyclopentane | 1.9E−02 | | 1.2E−03 | 5.0E−06 | | | | | | | | | |
| 2,2-dimethylbutane | 4.4E−03 | | 3.2E−02 | 1.9E−11 | | | | | | | | | |
| 2-methylpentane | 3.8E−02 | | 5.1E−03 | 2.0E−08 | | | | | | | | | |
| n-hexane | 1.4E−02 | | 2.0E−04 | 2.1E−09 | | | | | | | | | |
| Methylcyclopentane | 1.8E−03 | | 2.9E−05 | 6.5E−11 | | | | | | | | | |

TABLE 1-continued

| Stream names | Targeted effluents naphtha complex sent to TO | | | | | | TO section[1] | | | | WHB section | | |
|---|---|---|---|---|---|---|---|---|---|---|---|---|---|
| | NHT Stripper column off-gas | Regenerator off-gas stream | C5/C6 Stabilizer off-gas | C4 isomerization stabilizer off-gas | NHT Sour Water | Combustion Air | Quench Air | Make-up Natural Gas | Flue gas outlet TO section | Flue gas outlet WHB section | BFW in | Steam out | Condensate |
| Benzene TOTAL, kmol/h | 8.5E-04 78.34 | — 12.50 | — 131.97 | — 28.06 | — 449.72 | — 3870.32 | — 1447.07 | — 0.00 | — 6050.85 | — 6050.85 | — 4030.00 | — 3951.00 | — 79.00 |

Note 1:
the TO section is not optimized from an O2 level.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

It should be appreciated and understood by those of ordinary skill in the art that various other components such as valves, pumps, filters, coolers, etc., were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Specific Embodiments

While the following is described in conjunction with specific embodiments, it will be understood that this description is intended to illustrate and not limit the scope of the preceding description and the appended claims.

A first embodiment of the invention is a process for treating off-gas and water effluent streams in a naphtha complex comprising thermally oxidizing at least one of a NHT stripper off-gas stream from a NHT stripper, a $C_5$-$C_6$ isomerization stabilizer off-gas stream from a $C_5$-$C_6$ isomerization stabilizer column, a regenerator off-gas stream from a catalyst regenerator zone of reforming zone, a $C_4$ isomerization stabilizer off-gas stream from a $C_4$ isomerization stabilizer column, and a NHT sour water stream from a NHT product separator in a thermal oxidation system, comprising thermally oxidizing the at least one of the NHT stripper off-gas stream, the $C_5$-$C_6$ isomerization stabilizer off-gas stream, the regenerator off-gas stream, the $C_4$ isomerization stabilizer off-gas stream, and the NHT sour water stream in a thermal oxidizing section forming flue gas consisting essentially of at least one of $H_2O$, $CO_2$, $N_2$, $O_2$, SOx, NOx, HCl, $Cl_2$, dioxins, and furans; optionally recovering waste heat from the flue gas in an optional waste heat recovery section; removing at least one of SOx, HCl, and $Cl_2$ from the flue gas in a SOx removal section to form a de-SOx outlet flue gas consisting essentially of at least one of $H_2O$, $CO_2$, $N_2$, $O_2$, NOx, dioxins, and furans, wherein removing the at least one of SOx, HCl, and $Cl_2$ from the flue gas comprises quenching the flue gas in a quench section to form quenched flue gas after recovering the waste heat; and contacting a caustic solution or an $NH_3$ based solution with the quenched flue gas in a scrubbing section to form the de-SOx outlet flue gas and a liquid stream comprising at least one of $H_2O$, $Na_2SO_3$, $Na_2SO_4$, $Na_2HSO_3$, $Na_2CO_3$, NaCl, $(NH_4)_2SO_4$. and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, Ca$(NO_3)_2$, $MgCl_2$, $MgCO_3$, $MgSO_4$, $Mg(NO_3)_2$, Cl2, NOx, dioxins, and furans, wherein the reactant comprises at least one of $NaHCO_3$, $NaHCO_3.Na_2CO_3.2(H_2O)$, $CaCO_3$, $Ca(OH)_2$, and $Mg(OH)_2$; and filtering the reaction section flue gas in a filtration section to remove NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$ to form the de-SOx outlet flue gas; optionally removing NOx from the de-SOx outlet flue gas in a NOx removal section to form a de-NOx outlet flue gas consisting essentially of at least one of $H_2O$, $CO_2$, $N_2$, $O_2$, dioxins, and furans; and optionally removing dioxin, furan, or both from the de-SOx outlet flue gas or the de-NOx outlet flue gas in a dioxin-furan removal section to form a treated outlet flue gas consisting essentially of at least one of $H_2O$, $CO_2$, $N_2$, $O_2$, HCl, and $Cl_2$. An embodiment of the invention is one, any or all of prior embodiments in this paragraph up through the first embodiment in this paragraph wherein the thermal oxidizing section comprises an adiabatic thermal oxidizer chamber or a non-adiabatic direct fired boiler. An embodiment of the invention is one, any or all of prior embodiments in this paragraph up through the first embodiment in this paragraph wherein removing the dioxin, furan, or both comprises removing the dioxin, furan, or both using a catalyst or by co-injecting activated carbon with dry sorbent. An embodiment of the invention is one, any or all of prior embodiments in this paragraph up through the first embodiment in this paragraph further comprising providing the recovered waste heat to at least one piece of equipment in the naphtha complex. An embodiment of the invention is one, any or all of prior embodiments in this paragraph up through the first embodiment in this paragraph wherein the NOx removal section and the dioxin-furan removal section are present. An embodiment of the invention is one, any or all of prior embodiments in this paragraph up through the first embodiment in this paragraph wherein the NOx removal section is present and the dioxin-furan removal section is not present. An embodiment of the invention is one, any or all of prior embodiments in this paragraph up through the first embodiment in this paragraph wherein the dioxin-furan removal section is present and the NOx removal section is not present. An embodiment of the invention is one, any or all of prior embodiments in this paragraph up through the first embodiment in this paragraph wherein the NOx removal section and the dioxin-furan removal section are not present. An embodiment of the invention is one, any or all of prior embodiments in this paragraph up through the first embodiment in this paragraph further comprising separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, HCl, and molecules having 4 carbon atoms or less, and a $C_5$-$C_6$ isomerization stabilizer bottoms stream comprising molecules having 4 carbon atoms or more; and thermally oxidizing the NHT stripper off-gas stream, the $C_5$-$C_6$ isomerization stabilizer off-gas stream, or both in the thermal oxidation system. An embodiment of the invention is one, any or all of prior embodiments in this paragraph up through the first embodiment in this paragraph further comprising reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system. An embodiment of the invention is one, any or all of prior embodiments in this paragraph up through the first embodiment in this paragraph further comprising isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system. An embodiment of the invention is one, any or all of prior embodiments in this paragraph up through the first embodiment in this paragraph further comprising before separating the naphtha stream in the NHT stripper column hydrotreating a naphtha feed stream comprising molecules having 5 to 12 carbon atoms in a naphtha hydrotreating zone to form a hydrotreated naphtha stream; separating the NHT sour water stream comprising $H_2$, $NH_3$ and $H_2S$ from the hydrotreated naphtha stream in the NHT product separator to form a dewatered hydrotreated naphtha stream, and wherein the dewatered hydrotreated naphtha stream comprises the naphtha stream; and thermally oxidizing the NHT sour water stream in the thermal oxidation system. An embodiment of the invention is one, any or all of prior embodiments in this paragraph up through the first embodiment in this paragraph further comprising reforming a naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system. An embodiment of the invention is one, any or all of prior embodiments in this paragraph up through the first embodiment in this paragraph further comprising isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system. An embodiment of the invention is one, any or all of prior embodiments in this paragraph up through the first embodiment in this paragraph further comprising isomerizing a $C_4$ feed stream in a $C_4$ isomerization zone in the presence of an $C_4$ isomerization catalyst under $C_4$ isomerization conditions to convert n-butane to isobutane and form an $C_4$ isomerization outlet stream comprising isomerized $C_4$ molecules; separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system. An embodiment of the invention is one, any or all of prior embodiments in this paragraph up through the first embodiment in this paragraph further comprising hydrotreating a naphtha feed stream comprising molecules having 5 to 12 carbon atoms in a naphtha hydrotreating zone to form a hydrotreated naphtha stream; separating the NHT sour water stream comprising Hz, $NH_3$, and $H_2S$ from the hydrotreated naphtha stream in the NHT product separator to form a dewatered hydrotreated naphtha stream, and wherein the dewatered hydrotreated naphtha stream comprises the naphtha stream; separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, HCL, $Cl_2$, and molecules having 4 carbon atoms or less, and a $C_5$-$C_6$ isomerization stabilizer bottoms stream comprising molecules having 4 carbon atoms or more; and thermally oxidizing at least one of the NHT stripper off-gas stream, the $C_5$-$C_6$ isomerization stabilizer off-gas stream, and the NHT sour water stream in the thermal oxidation system. An embodiment of the invention is one, any or all of prior embodiments in this paragraph up through the first embodiment in this paragraph further comprising hydrotreating a naphtha feed stream comprising molecules having 5 to 12 carbon atoms in a naphtha hydrotreating zone to form a hydrotreated naphtha stream; separating the NHT sour water stream comprising $H_2$, HN3 and $H_2S$ from the hydrotreated naphtha stream in the NHT product separator to form a naphtha stream; and thermally oxidizing the NHT sour water stream in the thermal oxidation system. An embodiment of the invention is one, any or all of prior embodiments in this paragraph up through the first embodiment in this paragraph further comprising separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream; separating the $C_5$-$C_6$ isomerization outlet stream in a $C_5$-$C_6$ isomerization stabilizer column into the $C_5$-$C_6$ isomerization stabilizer off-gas stream consisting essentially of at least one of $H_2$, HCl, $Cl_2$, and molecules having 4 carbon atoms or less, and a $C_5$-$C_6$ isomerization stabilizer bottoms stream comprising molecules having 4 carbon atoms or more; and thermally oxidizing the NHT stripper off-gas stream, the $C_5$-$C_6$ isomerization stabilizer off-gas stream, or both in the thermal oxidation system. An embodiment of the invention is one, any or all of prior embodiments in this paragraph up through the first embodiment in this paragraph further comprising reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system. An embodiment of the invention is one, any or all of prior embodiments in this paragraph up through the first embodiment in this paragraph further comprising separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more; separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms; reforming the naphtha splitter bottoms stream in a catalytic reforming zone in the presence of a reforming catalyst to form reformate product comprising a mixture of paraffin, naphthene, and aromatic molecules having 5 carbon atoms or more; regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the NHT stripper off-gas stream, the regenerator off-gas stream, or both in the thermal oxidation system.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for treating off-gas and water effluent streams in a naphtha complex comprising:
    thermally oxidizing at least one of a NHT stripper off-gas stream from a NHT stripper column, a $C_5$-$C_6$ isomerization stabilizer off-gas stream from a $C_5$-$C_6$ isomerization stabilizer column, a regenerator off-gas stream from a continuous catalyst regeneration zone of a reforming zone, a $C_4$ isomerization stabilizer off-gas stream from a $C_4$ isomerization stabilizer column, and a NHT sour water stream from a NHT product separator in a thermal oxidation system, comprising:
        thermally oxidizing the at least one of the NHT stripper off-gas stream, the $C_5$-$C_6$ isomerization stabilizer off-gas stream, the regenerator off-gas stream, the $C_4$ isomerization stabilizer off-gas stream, and the NHT sour water stream in a thermal oxidizing section forming flue gas consisting essentially of at least one of $H_2O$, $CO_2$, $N_2$, $O_2$, SOx, NOx, HCl, $Cl_2$, dioxins, and furans;
        optionally recovering waste heat from the flue gas in a waste heat recovery section;
        removing at least one of SOx, HCl, and $Cl_2$ from the flue gas in a SOx removal section to form a de-SOx outlet flue gas consisting essentially of at least one of $H_2O$, $CO_2$, $N_2$, $O_2$, NOx, dioxins, and furans, wherein removing the at least one of SOx, HCl, and Cl$_2$ from the flue gas comprises:
quenching the flue gas in a quench section to form quenched flue gas after recovering the waste heat; and
contacting a caustic solution or an NH$_3$ based solution with the quenched flue gas in scrubbing section to form the de-SOx outlet flue gas and a liquid stream comprising at least one of H$_2$O, Na$_2$SO$_3$, Na$_2$SO$_4$, Na$_2$HSO$_3$, Na$_2$CO$_3$, NaCl, (NH$_4$)$_2$SO$_4$, and NH$_4$Cl;
or
reacting the flue gas with a reactant in an SOx reaction section to form a reaction section flue gas consisting essentially of at least one of H$_2$O, CO$_2$, N$_2$, O$_2$, NaCl, Na$_2$CO$_3$, Na$_2$SO$_4$, NaNO$_3$, CaCl$_2$, CaSO$_4$, CaCO$_3$, Ca(NO$_3$)$_2$, MgCl$_2$, MgCO$_3$, MgSO$_4$, Mg(NO$_3$)$_2$, Cl$_2$, NOx, dioxins, and furans, wherein the reactant comprises at least one of NaHCO$_3$, NaHCO$_3$.Na$_2$CO$_3$.2(H$_2$O), CaCO$_3$, Ca(OH)$_2$, and Mg(OH)$_2$; and
filtering the reaction section flue gas in a filtration section to remove NaCl, Na$_2$CO$_3$, Na$_2$SO$_4$, NaNO$_3$, CaCl$_2$, CaSO$_4$, CaCO$_3$, Ca(NO$_3$)$_2$, MgCl$_2$, MgCO$_3$, MgSO$_4$, and Mg(NO$_3$)$_2$ to form the de-SOx outlet flue gas;
optionally removing NOx from the de-SOx outlet flue gas in an NOx removal section to form a de-NOx outlet flue gas consisting essentially of at least one of H$_2$O, CO$_2$, N$_2$, O$_2$, dioxins, and furans; and
optionally removing dioxin, furan, or both from the de-SOx outlet flue gas or the de-NOx outlet flue gas in a dioxin-furan removal section to form a treated outlet flue gas consisting essentially of at least one of H$_2$O, CO$_2$, N$_2$, O$_2$, HCl, and Cl$_2$.

2. The process of claim 1 wherein the thermal oxidizing section comprises an adiabatic thermal oxidizer chamber or a non-adiabatic direct fired boiler.

3. The process of claim 1 wherein the dioxin, furan, or both comprises removing the dioxin, furan, or both using a catalyst or by co-injecting activated carbon with dry sorbent upstream of the dioxin-furan removal section.

4. The process of claim 1 further comprising:
providing the recovered waste heat to at least one piece of equipment in the naphtha complex.

5. The process of claim 1 wherein the NOx removal section and the dioxin-furan removal section are present.

6. The process of claim 1 wherein the NOx removal section is present and the dioxin-furan removal section is not present.

7. The process of claim 1 wherein the dioxin-furan removal section is present and the NOx removal section is not present.

8. The process of claim 1 wherein the NOx removal section and the dioxin-furan removal section are not present.

9. The process of claim 1 further comprising:
separating the naphtha stream comprising molecules having 1 to 12 carbon atoms in a NHT stripper column into at least a NHT stripper off-gas stream consisting essentially of at least one of H$_2$, H$_2$S, NH$_3$ and molecules having 5 carbon atoms or less, and a NHT stripper bottoms stream comprising molecules having five carbon atoms or more;
separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms;
isomerizing at least a portion of the naphtha splitter overhead stream in a C$_5$-C$_6$ isomerization zone in the presence of a C$_5$-C$_6$ isomerization catalyst under C$_5$-C$_6$ isomerization conditions to convert n-pentane to isopentane and n-hexane to isohexane to form an C$_5$-C$_6$ isomerization outlet stream;
separating the C$_5$-C$_6$ isomerization outlet stream in the C$_5$-C$_6$ isomerization stabilizer column into the C$_5$-C$_6$ isomerization stabilizer off-gas stream consisting essentially of at least one of H$_2$, HCl, and molecules having 4 carbon atoms or less, and a C$_5$-C$_6$ isomerization stabilizer bottoms stream comprising molecules having 4 carbon atoms or more; and
thermally oxidizing the NHT stripper off-gas stream, the C$_5$-C$_6$ isomerization stabilizer off-gas stream, or both in the thermal oxidation system.

10. The process of claim 9 further comprising:
reforming the naphtha splitter bottoms stream in a catalytic reforming zone in the presence of a reforming catalyst to form reformate product comprising a mixture of paraffin, naphthene, and aromatic molecules having 5 carbon atoms or more;
regenerating spent reforming catalyst in the continuous catalyst regeneration zone forming regenerated reforming catalyst and the regenerator off-gas stream consisting essentially of at least one of N$_2$, H$_2$O, CO$_2$, HCl, O$_2$, and Cl$_2$; and
recycling the regenerated reforming catalyst to the catalytic reforming zone; and
thermally oxidizing the regenerator off-gas stream in the thermal oxidation system.

11. The process of claim 10 further comprising:
isomerizing a C$_4$ feed stream in a C$_4$ isomerization zone in the presence of an C$_4$ isomerization catalyst under C$_4$ isomerization conditions to convert n-butane to isobutane to form an C$_4$ isomerization outlet stream comprising isomerized C$_4$ molecules;
separating the C$_4$ isomerization outlet stream in the C$_4$ isomerization stabilizer column into the C$_4$ isomerization stabilizer off-gas stream consisting essentially of H$_2$, N$_2$, HCl, and molecules having 4 carbon atoms or less, and a C$_4$ isomerization stabilizer bottoms stream comprising molecules having 4 carbon atoms or more; and
thermally oxidizing the C$_4$ isomerization stabilizer off-gas stream in the thermal oxidation system.

12. The process of claim 11 further comprising:
before separating the naphtha stream in the NHT stripper column:
hydrotreating a naphtha feed stream comprising molecules having 5 to 12 carbon atoms in a naphtha hydrotreating zone to form a hydrotreated naphtha stream;
separating the NHT sour water stream comprising H$_2$, NH$_3$ and H$_2$S from the hydrotreated naphtha stream in a NHT product separator to form a dewatered hydrotreated naphtha stream, and wherein the dewatered hydrotreated naphtha stream comprises the naphtha stream; and
thermally oxidizing the NHT sour water stream in the thermal oxidation system.

13. The process of claim 1 further comprising:
reforming a naphtha splitter bottoms stream in a catalytic reforming zone in the presence of a reforming catalyst to form reformate product comprising a mixture of paraffin, naphthene, and aromatic molecules having 5 carbon atoms or more;

regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system.

14. The process of claim 13 further comprising:

isomerizing a $C_4$ feed stream in a $C_4$ isomerization zone in the presence of an $C_4$ isomerization catalyst under $C_4$ isomerization conditions to convert n-butane to isobutane to form a $C_4$ isomerization outlet stream comprising isomerized $C_4$ molecules;

separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system.

15. The process of claim 1 further comprising:

isomerizing a $C_4$ feed stream in a $C_4$ isomerization zone in the presence of a $C_4$ isomerization catalyst under $C_4$ isomerization conditions to convert n-butane to isobutane and form a $C_4$ isomerization outlet stream comprising isomerized $C_4$ molecules;

separating the $C_4$ isomerization outlet stream in the $C_4$ isomerization stabilizer column into the $C_4$ isomerization stabilizer off-gas stream consisting essentially of $H_2$, $N_2$, HCl, and molecules having 4 carbon atoms or less, and a $C_4$ isomerization stabilizer bottoms stream comprising molecules having 4 carbon atoms or more; and thermally oxidizing the $C_4$ isomerization stabilizer off-gas stream in the thermal oxidation system.

16. The process of claim 15 further comprising:

hydrotreating a naphtha feed stream comprising molecules having 5 to 12 carbon atoms in a naphtha hydrotreating zone to form a hydrotreated naphtha stream;

separating the NHT sour water stream comprising $H_2$, $NH_3$, and $H_2S$ from the hydrotreated naphtha stream in the NHT product separator to form a dewatered hydrotreated naphtha stream, and wherein the dewatered hydrotreated naphtha stream comprises the naphtha stream;

separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more;

separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms;

isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream;

separating the $C_5$-$C_6$ isomerization outlet stream in the $C_5$-$C_6$ isomerization stabilizer column into the $C_5$-$C_6$ isomerization stabilizer off-gas stream consisting essentially of at least one of $H_2$, HCl, and molecules having 4 carbon atoms or less, and a $C_5$-$C_6$ isomerization stabilizer bottoms stream comprising molecules having 4 carbon atoms or more; and thermally oxidizing at least one of the NHT stripper off-gas stream, the $C_5$-$C_6$ isomerization stabilizer off-gas stream, and the NHT sour water stream in the thermal oxidation system.

17. The process of claim 1 further comprising:

hydrotreating a naphtha feed stream comprising molecules having 5 to 12 carbon atoms in a naphtha hydrotreating zone to form a hydrotreated naphtha stream;

separating the NHT sour water stream comprising $H_2$, $HN_3$, and $H_2S$ from the hydrotreated naphtha stream in the NHT product separator to form a naphtha stream; and thermally oxidizing the NHT sour water stream in the thermal oxidation system.

18. The process of claim 17 further comprising:

separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more;

separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms;

isomerizing at least a portion of the naphtha splitter overhead stream in a $C_5$-$C_6$ isomerization zone in the presence of a $C_5$-$C_6$ isomerization catalyst under $C_5$-$C_6$ isomerization conditions to convert n-pentane to isopentane and n-hexane to isohexane and form an $C_5$-$C_6$ isomerization outlet stream;

separating the $C_5$-$C_6$ isomerization outlet stream in the $C_5$-$C_6$ isomerization stabilizer column into the $C_5$-$C_6$ isomerization stabilizer off-gas stream consisting essentially of at least one of $H_2$, HCl, and molecules having 4 carbon atoms or less, and a $C_5$-$C_6$ isomerization stabilizer bottoms stream comprising molecules having 4 carbon atoms or more; and thermally oxidizing the NHT stripper off-gas stream, the $C_5$-$C_6$ isomerization stabilizer off-gas stream, or both in the thermal oxidation system.

19. The process of claim 18 further comprising:

reforming the naphtha splitter bottoms stream in a catalytic reforming zone in the presence of a reforming catalyst to form reformate product comprising a mixture of paraffin, naphthene, and aromatic molecules having 5 carbon atoms or more;

regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the regenerator off-gas stream in the thermal oxidation system.

20. The process of claim 17 further comprising:

separating the naphtha stream comprising molecules having 1 to 12 carbon atoms in a NHT stripper column into at least a NHT stripper off-gas stream consisting essentially of at least one of $H_2$, $H_2S$, $NH_3$ and molecules having 5 carbon atoms or less, and a NHT stripper bottoms stream comprising molecules having five carbon atoms or more;

separating the NHT stripper bottoms stream in a naphtha splitter column into a naphtha splitter overhead stream comprising molecules having 5-6 carbon atoms and a naphtha splitter bottoms stream comprising molecules having 6-12 carbon atoms;

reforming the naphtha splitter bottoms stream in a catalytic reforming zone in the presence of a reforming catalyst to form reformate product comprising a mixture of paraffin, naphthene, and aromatic molecules having 5 carbon atoms or more;

regenerating spent reforming catalyst in the continuous catalyst regeneration zone forming regenerated reforming catalyst and the regenerator off-gas stream consisting essentially of at least one of $N_2$, $H_2O$, $CO_2$, HCl, $O_2$, and $Cl_2$; and recycling the regenerated reforming catalyst to the catalytic reforming zone; and thermally oxidizing the NHT stripper off-gas stream, the regenerator off-gas stream, or both in the thermal oxidation system.

* * * * *